United States Patent [19]

Geyer

[11] 4,110,378

[45] Aug. 29, 1978

[54] METHOD OF REDUCTION EMPLOYING RESIN ADSORBENTS

[75] Inventor: Wolfgang G. Geyer, Glassboro, N.J.

[73] Assignee: Rohm and Haas Company, Philadelphia, Pa.

[21] Appl. No.: 691,273

[22] Filed: Jun. 1, 1976

Related U.S. Application Data

[62] Division of Ser. No. 583,821, Jun. 4, 1975, Pat. No. 3,975,155.

[51] Int. Cl.$^2$ .................. C07B 1/00; C07C 103/22
[52] U.S. Cl. .................. 260/558 S; 260/561 S; 260/690; 252/426
[58] Field of Search .................. 260/558 S, 690, 708, 260/302 A, 304 A, 557 R, 561 S; 252/426; 23/230 R, 230 M

[56] References Cited

U.S. PATENT DOCUMENTS

| | | | |
|---|---|---|---|
| 3,106,458 | 10/1963 | Grosskopf | 23/232 R |
| 3,159,632 | 12/1964 | Sargent | 260/708 X |
| 3,172,887 | 3/1965 | Bondi | 260/708 X |
| 3,351,487 | 11/1967 | Levine et al. | 427/306 X |
| 3,718,432 | 2/1973 | Roth | 23/230 R |
| 3,935,294 | 1/1976 | Teller | 252/426 X |

*Primary Examiner*—Winston A. Douglas
*Assistant Examiner*—Thomas A. Waltz
*Attorney, Agent, or Firm*—Bernard J. Burns; William E. Lambert, III; George W. F. Simmons

[57] ABSTRACT

This invention relates to a quantitative analytical method for the isolation and determination of 3-isothiazolones in aqueous or nonaqueous media.

The method involves isolating the isothiazolone by adsorbing it on a support; treating the isothiazolone with a reducing agent thereby cleaving the ring; reacting the resulting sulfhydryl group with a color forming reagent whose color development is directly proportional to the concentration of the isothiazolone and measuring the isothiazolone concentration via a calibrated color comparator or colorimeter.

1 Claim, No Drawings

METHOD OF REDUCTION EMPLOYING RESIN ADSORBENTS

This is a division of application Ser. No. 583,821 filed June 4, 1975 now U.S. Pat. No. 3,975,155 granted Aug. 17, 1976.

SUMMARY OF THE INVENTION

This invention relates to a quantitative method for the determination of microlevel concentrations of substituted and unsubstituted 3-isothiazolones in aqueous or nonaqueous media. Various substituted 3-isothiazolones are described in the literature and have found widespread usage in commercial and industrial applications. These compounds have been used as algaecides in swimming pools, slimicides in cooling tower water, and act as preservatives in metal working fluids. They have also found applications in paper mill white water, sheep dip water, and in tannery, agricultural, cosmetic and pharmaceutical compositions.

A quantitative method for determining 3-isothiazolone concentrations at microlevels which does not involve gas chromatography (GC) or ultraviolet (UV) spectrophotometry is especially valuable for field test applications. Such instrumental methods of analysis are highly impractical and costly to transport and set up for field test applications. The colorimetric method of this invention for the detection of microquantities of 3-isothiazolones is portable, requires a minimum of equipment, is fast, accurate, reproducible and inexpensive.

In particular, this invention relates to the adsorption of a 3-isothiazolone on a suitable support and the reductive cleavage of the isothiazolone ring while still adsorbed on the support. The reduced isothiazolone is then removed from the support and reacted with a color forming reagent. The original concentration of the isothiazolone is then determined by colorimetry.

The adsorption of a compound on a suitable support and the reduction of said compound while still adsorbed on the support is not meant to be limited to 3-isothiazolones. The method of this invention can be applied to the reduction of any organic compound containing a functional group that can be adsorbed on a suitable support and reduced while still adsorbed on the support. Typical functional groups which can be reduced by metal hydride reductions include the following:

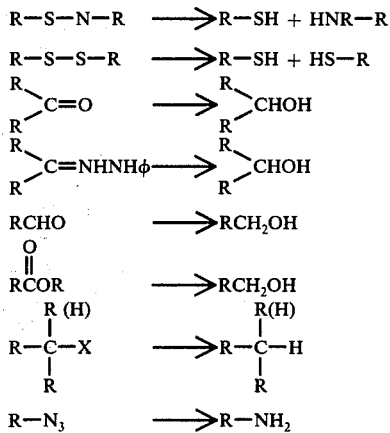

This method of adsorbing a compound on a suitable support prior to reducing it while still adsorbed on the support possesses many advantages. The adsorption of the compound on the support can eliminate the presence of other compounds which would interfere or compete with the reduction of the compound. It reduces the volume of the reduction reaction since the compound is concentrated on the support. Finally, it facilitates the recovery of the reduced product in a pure state since all other interfering substances have been removed before the reduction step takes place. The method of particular interest however, is the adsorption of substituted 3-isothiazolones on a suitable support and the reductive cleavage of the sulfur-nitrogen bond with a metal hydride while still adsorbed on the support.

The preferred isothiazolones which can be analyzed via this method are those of the formula:

wherein R is a hydrogen atom, an unsubstituted or substituted alkyl group of 1 to 10 carbon atoms, an unsubstituted or substituted cycloalkyl group of 3 to 8 carbon atoms, an unsubstituted or substituted aralkyl group of up to 10 carbon atoms or an unsubstituted or substituted aryl group of up to 10 carbon atoms; X and Y are independently a hydrogen atom, a halogen atom or a ($C_1$-$C_4$) alkyl group or when taken together form a substituted or unsubstituted benzene ring to give a compound of the formula:

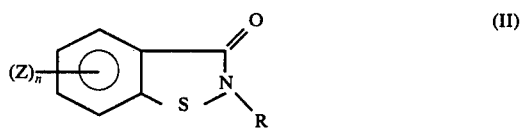

wherein Z is a ($C_1$-$C_4$) alkyl group, a ($C_1$-$C_4$) alkoxyl group, a cyano group, a nitro group or a halogen atom; and n is an integer from zero to two.

The metal salt complexes and acid addition salts of the above 3-isothiazolones having the general formula

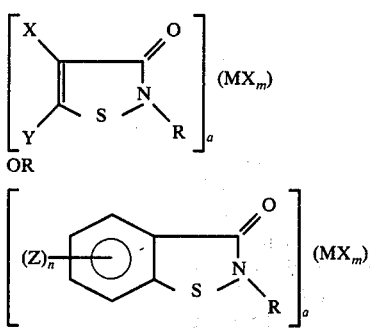

wherein R, X, Y, Z and n are as defined above. M is a cation of barium, cadmium, calcium, chromium, cobalt, copper, iron lead, lithium, magnesium, manganese, mercury, nickel, silver, sodium, strontium, tin, or zinc, or a complex of the cation with ammonia or an organic amine. X is an anion selected from chloride, bromide, iodide, sulfate, nitrate, acetate, perchlorate, bisulfate, bicarbonate, oxalate, malate, p-toluenesulfonate, carbonate, phosphate and the like. The subscript a is an integer of 1 or 2 and the subscript m is an integer chosen such that the valence of the anion X satisfies the valence of the cation M.

Typical reducing agents which can be utilized in the reductive cleavage of the isothiazolone ring structure include such reagents as sodium borohydride, lithium borohydride, alkyl aluminum hydride and the like. The preferred reducing agent being an aqueous solution of sodium borohydride.

Although, the preferred method for cleaving the isothiazolone ring is by a reductive cleavage, the isothiazolone ring can also be cleaved by nucleophilic attack on the sulfur by a strong anion such as hydroxide ion, sulfide ion and the like.

Solvents which can be used to remove the cleaved compound from the support include solvents such as methanol, ethanol, ketones and the like and aqueous mixtures thereof.

The color forming reagents which can be utilized in this invention include 5,5'-dithiobis(2-nitrobenzoic acid), bis(p-nitrophenyl)disulfide, 2,2'-dithiobis-(5-nitropyridine), and the like.

Typical supports which can be utilized in the practice of this invention include macroreticular styrene-divinyl benzene adsorbent resins (such as those sold under the trademarks Amberlite ® XAD-4, XAD-2, and XAD-1 or Porapak ® Q).

These supports can be used in packed columns, thin layer sheets or as flocculants in the media to be analyzed but are preferably used as a packing in a column.

The isolation of these isothiazolones from nonaqueous media can be accomplished with appropriate modifications whereby the isothiazolone is first isolated from the nonaqueous media e.g., by organic solvents which are removed for example by evaporation before the isothiazolone is adsorbed on the support from an aqueous solution.

Examples of the nonaqueous media from which these isothiazolones can be isolated include mineral oil based metal working fluids (such as those sold under the trademark Griton ® 1300), triethanolamine based water soluble metal working fluids (such as those sold under the trademark Hamikleer ®), cosmetic and/or pharmaceutical preparations such as creams, lotions, ointments, salves and the like.

A preferred embodiment of this invention is a quantitative method for the colorimetric determination of the concentration of substituted and unsubstituted isothiazolones in aqueous and nonaqueous media which involves: (a) adsorbing the isothiazolone of Formula I or Formula II on a polymeric macroreticular resin adsorbant packed column; (b) reductively cleaving the isothiazolone ring with a reducing agent such as sodium borohydride while still adsorbed on the column; (c) removing the thiol which is formed by eluting it off the column with a protic solvent such as methanol; and (d) forming a colored solution by adding a color forming reagent such as 5,5'-dithio-bis(2-nitrobenzoic acid), the color development being directly related to the concentration of the isothiazolone. The concentration of the original isothiazolone can be measured either visually with a calibrated color comparator or instrumentally with a colorimeter.

The most preferred embodiment of this invention is a quantitative method for the colorimetric determination of 2-methyl-5-chloro-4-isothiazolin-3-one calcium chloride complex in aqueous media which involves the following steps:

(a) adsorbing the isothiazolone on an Amberlite ® XAD-4 resin packed column;
(b) reductively cleaving the isothiazolone ring with sodium borohydride while still adsorbed on the column;
(c) removing the thiol which is formed by eluting it off the column with methanol; and
(d) forming a colored solution by adding a color forming reagent such as 5,5'-dithiobis-(2-nitro-benzoic acid).

Another preferred embodiment of this invention is the selective reductive cleavage of an isothiazolone ring by first adsorbing the isothiazolone on a suitable support and then reducing it with a reducing agent such as sodium borohydride, alkyl aluminum hydride and the like.

The following is the proposed generalized reaction sequence which occurs in the process for the determination of the isothiazolones of this invention.

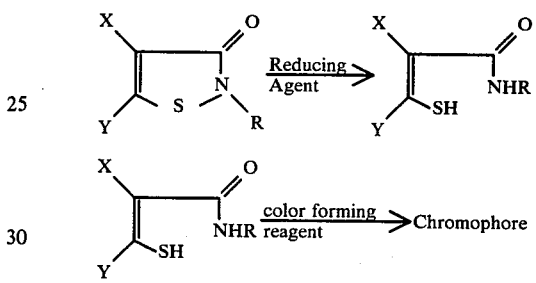

The following examples are presented to illustrate the quantitative colorimetric method of the present invention. These examples are provided merely to demonstrate the operation of the present invention and are not to be considered as limitations thereof.

EXAMPLE I

General Procedure For Separating Isothiazolones

In this method microquantities of isothiazolone in cooling tower water, metal working fluids and swimming pool water can be estimated by visual comparison of reacted test solutions. Zero to 10 ppm of isothiazolone can be measured by the following general method of this invention.

Ten to 100 micrograms of isothiazolone, dissolved in 3-100 ml. of water are adsorbed on 150-300 mg. of 50-80 mesh Amberlite ® XAD-4 resin. The isothiazolone is then reduced in situ on the column with 1.0 mg. of sodium borohydride in 0.5 ml of water. The excess reagent is removed by a water wash then, after elution with 2.5 ml of methanol, it is reacted with 1 ml of 5,5'-bisdithio(2-nitrobenzoic acid) in 1.0 ml of pH 8.0 buffer solution to form a yellow colored solution. This solution is compared to a calibrated standard or measured by a spectrophotometer. Minor changes of the basic test must be made for analyzing metal working fluids or if free chlorine or hypochlorite is present. The presence of nitrate does not interfere with this determination.

EXAMPLE II

Separation of 2-Methyl-5-chloro-4-isothiazolin-3-one Calcium Chloride Complex from Cooling Tower Water To 10 ml. of cooling tower water, 5 ppm of isothiazolone and 5 ppm of Hyamine ® 3500, a quaternary biocide, are added. No interference is experienced when the sample is analyzed.

The cooling tower blank shows no color, even when treated with a sodium dichromate corrosion inhibitor (sold under the trademark Hagatreat®)) and a n-($C_{10}$-$C_{16}$) alkyl dimethylbenzylammonium chloride bis-tri-n-butyl tin oxide biocide (sold under the trademark Hagacide® 204).

EXAMPLE III

Separation of 2-Methyl-5-chloro-4-isothiazolin-3-one Calcium Chloride Complex from Griton® 1300

One part of Griton® 1300 metal working fluid is diluted with 20 parts of water and a milky white emulsion is formed. To two such samples is added 10 and 25 ppm of isothiazolone respectively. Without further treatment, 10 ml of the 10 ppm or 3 ml of the 25 ppm sample are passed through the Amberlite® XAD-4 resin. After the initial sample is passed through the column, the packing is flushed with 50 ml of $H_2O$ to remove any residual emulsion from the resin. Omitting the step obscures the test results due to the turbidity of the solution. Following the wash, 1.0 mg $NaBH_4$ in 0.5 ml $H_2O$ is added and the test is completed in the described manner of Example I with both concentrations.

EXAMPLE IV

Separation of 2-Methyl-5-chloro-4-isothiazolin-3-one Calcium Chloride Complex from Hamikleer®

One part of Hamikleer® metal working fluid is diluted with 40 parts of water and a clear amber colored solution is formed. To two such solutions is added 10 ppm and 25 ppm of isothiazolone respectively. These solutions are then tested, in a manner similar to the Griton® 1300 samples, including the washing prior to the $NaBH_4$ addition. With both the 10 ppm and the 25 ppm samples, recovery is quantitative.

EXAMPLE V

Separation of 2-Methyl-5-chloro-4-isothiazolin-3-one Calcium Chloride Complex from Paper Mill White Water Synthetic "white water" is used for this test. Common contaminants are added at twice the expected concentration prior to the test (indicated by *).
The composition is as follows:
0.3% $KH_2PO_4$
0.1% HT clay (Georgia kaolin)
0.1% soluble starch
0.1% ground wood pulp
30 ppm alum
*40 ppm Parez® 607 (6% T.S.) — a dry powdered melamine-formaldehyde resin for improving the wet and dry strength properties of paper.
*10 ppm Kymene® WS-557 (10% T.S.)—a cationic polyamide polyamine epichlorohydrin resin used in the manufacture of wet strength paper.
*10 ppm Pexol® 200 sizing agent—a fortified maleic anhydride adduct of sodium rosinate used as a sizing agent for paper.
*4 ppm Tamol® SN—a sodium salt of sulfonated naphthalene formaldehyde condensate dispersing agent.
5 ppm 2-methyl-5-chloro-4-isothiazolin-3-one calcium chloride complex.
The additives indicated by an asterisk are tested individually with and without isothiazolone where the isothiazolone level is 5 ppm. No interferences are experienced.

To examine the "white water" composite, it is first necessary to centrifuge a portion of the sample or to allow the suspended solids to settle on standing overnight. The clear solutions analyze without interference.

EXAMPLE VI

Separation of 2-Methyl-5-chloro-4-isothiazolin-3-one Calcium Chloride Complex from Swimming Pool Water In this procedure 100 ml portions of isothiazolone treated swimming pool water are tested. There is no evidence of interference and results compare favorably with gas chromatographic (GC) values.

The addition of 2 ppm of sodium hypochlorite (equivalent to about 1 ppm of chlorine), to 1 ppm of isothiazolone causes the test to fail by destroying the $NaBH_4$ reducing agent. The interference can be avoided by pre-treatment of the specimen with 5 mg of solid potassium iodide to liberate iodine which can then be reacted with 0.5 ml of 0.1 N sodium thiosulfate. The treated solution is passed through the Amberlite® XAD-4 column and the test is completed in the usual manner. Recovery of the added isothiazolone is quantitative. Direct addition of 100 ppm of sodium thiosulfate without prior KI treatment fails to avoid the interference.

EXAMPLE VII

Spectrophotometric Correlation

A typical set of five isothiazolone concentrations covering the range from 0–10 ppm in 2 ppm increments produces a nearly straight line relationship between concentration and absorbance when treated as described and measured with a spectrophotometer. The values are reproducible within experimental error indicating that the reaction is quantitative. When used with 100 ml sample solutions, which is typical for swimming pools, the straight line relationship is maintained. Typical test results are as follows:

| Concentration (ppm) | Absorbance (1 cm cell path) |
|---|---|
| 2 | 0.158 |
| 4 | 0.305 |
| 6 | 0.448 |
| 8 | 0.584 |
| 10 | 0.736 |

EXAMPLE VIII

Colorimetric Field Test — GC Correlation

Test results of swimming pool water samples are in good agreement with values obtained by a gas chromatograph with an electron capture detector. Both procedures are calibrated with the same standard solutions and the tests are performed on the same day.

| | 2-methyl-5-chloro-4-isothiazolin-3-one $CaCl_2$ | |
|---|---|---|
| Sample No. | Field Test | GC |
| 1 Before treatment | 0.3 | 0.1 |
| 2 1 hour after treatment | 1.0 | 1.0 |
| 3 Before treatment | 0.4 | 0.3 |
| 4 1 hour after treatment | 1.1 | 1.3 |
| 5 Before treatment | 0.3 | 0.3 |
| 6 1 hour after treatment | 1.0 | 0.9 |
| 7 Before Treatment | 0.3 | 0.2 |

| Sample No. | 2-methyl-5-chloro-4-isothiazolin-3-one CaCl$_2$ | |
|---|---|---|
| | Field Test | GC |
| 8 1 hour after treatment | 1.0 | 1.0 |

EXAMPLE IX

Validity of the Colorimetric Test for Other Isothiazolones

Solutions are prepared containing 5 ppm of 2-methyl-5-chloro-4-isothiazolin-3-one, 2-n-octyl-4-isothiazolin-3-one, 2-cyclohexyl-4,5-dichloro-4-isothiazolin-3-one, Proxel® CRL (23% solution of 4,5-benzisothiazolin-3-one) and 4,5-benzisothiazolin-3-one. The solutions are carried through the test as described above in Example I and their molar absorptivities (a) determined. Three out of the five compounds tested were in good agreement, allowing for the crudeness of the equipment. Proxel® CRL and 4,5-benzisothiazolin-3-one yield values almost exactly twice as high as the others. This may suggest that both the thionitrobenzoate anion and the benzisothiazolone product absorb at the same wavelength.

The measured molar absorptivity values are as shown, calculated in the manner given.

$$a = AM/bc$$

where $A$ = absorbance, $b$ = cell path, $c$ = *concentration in grams/liter*, $M$ = molecular weight, $a$ = molar absorptivity.

| Compound Tested | molar absorptivities (a) $\times 10^3$ |
|---|---|
| 2-methyl-5-chloro-4-isothiazolin-3-one CaCl$_2$ | 7.2 |
| 2-n-octyl-4-isothiazolin-3-one | 6.4 |
| 2-cyclohexyl-4,5-dichloro-4-isothiazolin-3-one | 7.6 |
| Proxel®CRL | 13.5 |
| 4,5-benzisothiazolin-3-one (reagent grade) | 14.8 |

The method for the detection of isothiazolones of this invention has a wide range of applicability. As shown above this invention can be used to determine microlevel concentrations of isothiazolones in cooling tower water, swimming pool water, paper mill white water, sheep dip water, tannery effluents, agricultural run-off, metal working fluids, and cosmetic and pharmaceutical preparations such as creams, lotions, ointments, salves and the like. Furthermore, the method of adsorbing a compound containing a reducible functional group on a macroreticular adsorbant and the reduction of the function group while still adsorbed on the adsorbant can be utilized in various other applications which suggest themselves to one skilled in the art.

I claim:

1. A method for the reduction of a reducible functional group selected from —S—N—, —S—S—, >C=O, >C=NHNH—, —CHO,

and —N$_3$ which comprises adsorbing the organic compound containing said reducible functional group on a polymeric macroreticular resin adsorbent and reducing the adsorbed functional group with an aqueous solution of sodium borohydride.

* * * * *